United States Patent [19]

Diaz

[11] 4,305,161
[45] Dec. 15, 1981

[54] URINATING AID FOR WOMEN

[76] Inventor: Rudy J. Diaz, 6516 W. 4th Ave., Hialeah, Fla. 33012

[21] Appl. No.: 146,120

[22] Filed: May 2, 1980

[51] Int. Cl.³ .................... A61G 9/00; B65D 33/00
[52] U.S. Cl. .................................... 4/144.2; 4/285; 128/295; 229/53; 248/99
[58] Field of Search ................ 4/144.1–144.4, 4/259, 274, 285, 315, 114.01; 128/295, 761, 767; 248/99; 229/53

[56] References Cited

U.S. PATENT DOCUMENTS

| 1,760,752 | 5/1930 | Happer | 248/99 |
| 2,734,198 | 2/1956 | Kutsche | 4/144.3 X |
| 3,403,410 | 10/1968 | Benzel et al. | 4/144.2 |
| 3,575,225 | 4/1971 | Muheim | 4/144.3 X |
| 3,679,125 | 7/1972 | Forance et al. | 248/99 X |
| 3,847,332 | 11/1974 | Murai | 248/99 |
| 3,920,179 | 11/1975 | Hall | 4/144.2 X |
| 4,069,994 | 1/1978 | Wharmby | 248/99 |
| 4,106,490 | 8/1978 | Spilman et al. | 128/761 |

FOREIGN PATENT DOCUMENTS 2533016 10/1977 Fed. Rep. of Germany ....... 4/144.1

Primary Examiner—Stuart S. Levy
Attorney, Agent, or Firm—Ernest H. Schmidt

[57] ABSTRACT

A disposable waterproof bag has a cuff-like fold at its upper end with side openings for the lateral reception of the opposed legs of a substantially rigid, wishbone-shaped support frame operative to maintain the mouth of the bag open while at the same time providing gripping means laterally outwardly of the bag opening to facilitate holding the open bag in position for urinating into while in standing position.

3 Claims, 6 Drawing Figures

U.S. Patent      Dec. 15, 1981      4,305,161
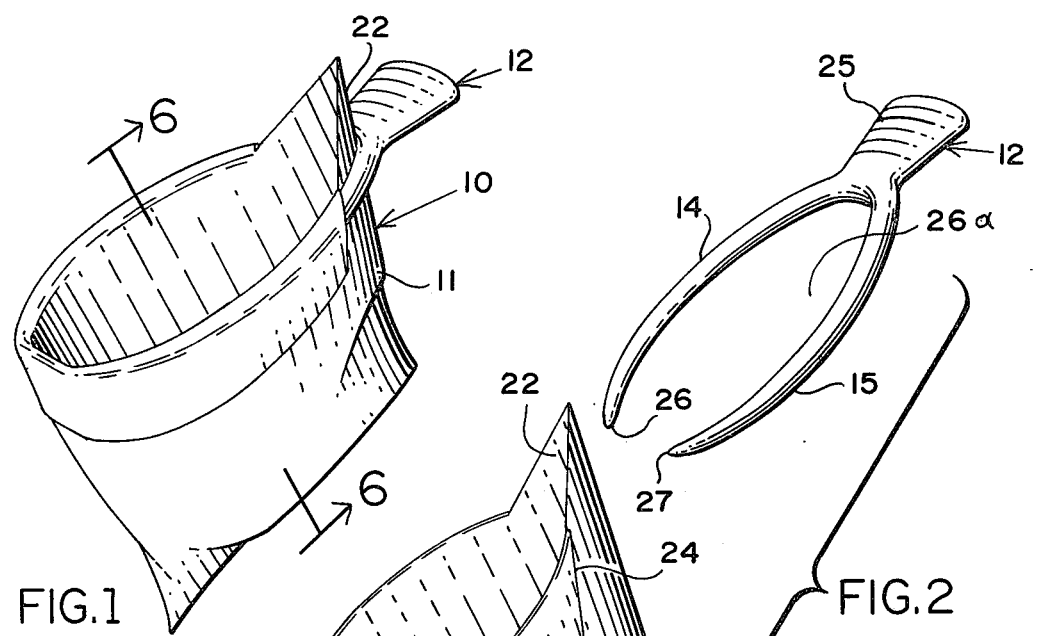
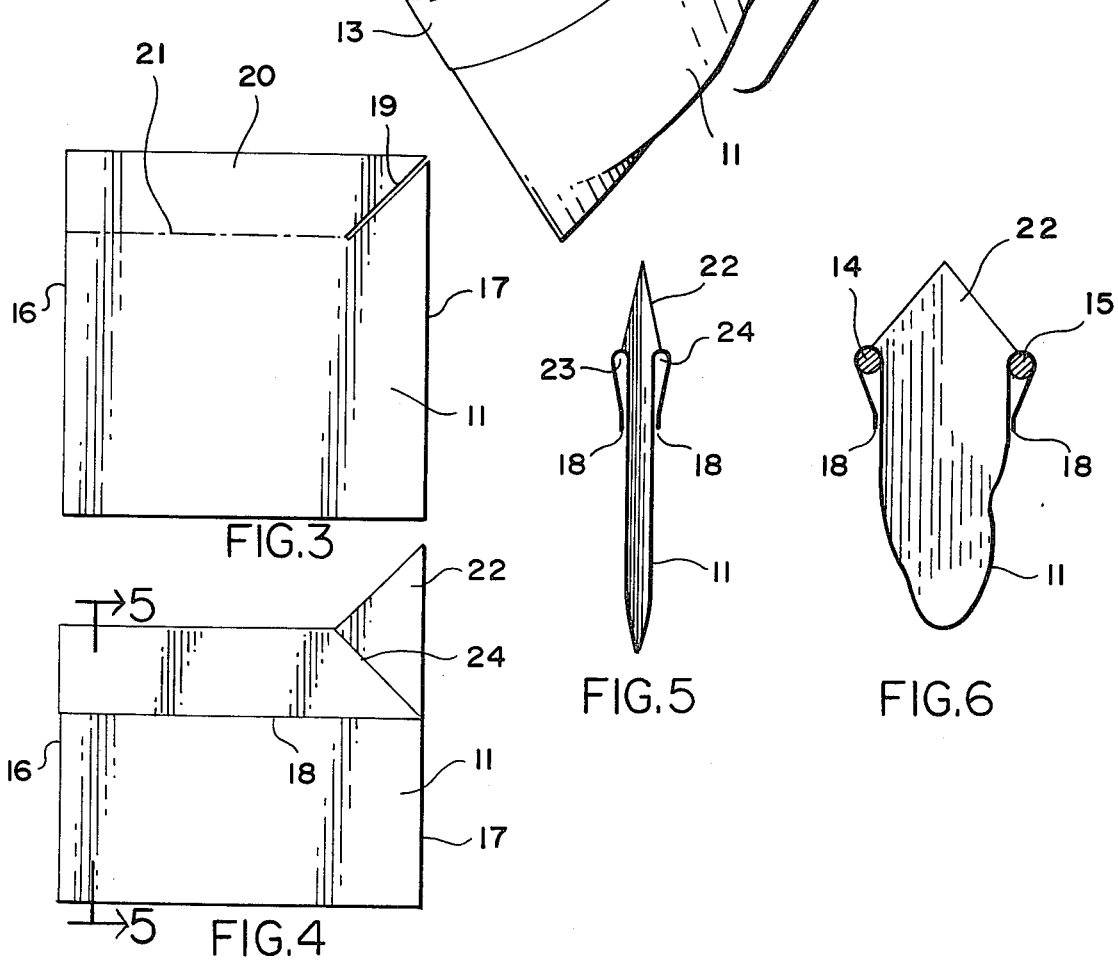

URINATING AID FOR WOMEN

BACKGROUND OF THE INVENTION

This invention relates to urinating aids for women, and is directed particularly to a disposable, waterproof bag for use in combination with a reusable, substantially rigid, manual support member for supporting the upper end of the bag in open position to facilitate urinating thereinto while standing.

Because it is often difficult to find clean and sanitary toilet facilities when away from home, particularly when travelling, women, because of the normal requirement for sitting down while urinating, often take measures to avoid direct contact with the toilet seat. This is usually done either by covering the seat with layers of paper towels or the like, or by assuming various squatting positions for urinating into a toilet bowl without contacting the toilet seat.

While various ambulatory female urinals of one kind or another have heretofore been devised for medical conditions such as incontinance, none is adaptable to occasional use by normal, healthy women for urinating directly into a disposable bag that is not attached in one way or another to the body of the user.

It is, accordingly, the principal object of this invention to provide a novel and improved women's urinating aid in the form of a flexible, light weight, waterproof bag for use in combination with reusable handle means attachable at the mouth of the bag for holding it in open condition to facilitate urinating thereinto while standing.

A more particular object is to provide a urinating aid of the character described wherein the flexible, waterproof bag is provided with a cuff-like marginal upper end portion having side openings for the insertion of a substantially rigid, wish-bone shaped support member adapted to hold the mouth of the bag open and thereby facilitate urinating thereinto while standing, whereafter the bag and contents can readily be pulled away from the support member for separate disposal.

Yet another object of the invention is to furnish a women's urinating aid of the above nature wherein the disposable bags are thin and flat enough to enable compact packaging for storage in a purse or handbag, and providing for ready dispensing one at a time as needed.

Still another object of the invention is to provide a women's urinating aid of the above nature which will be simple in structure, inexpensive to manufacture, convenient to apply and highly effective in use when travelling.

Other objects, features of the invention will be apparent from the following description when read with reference to the accompanying drawings.

BRIEF DESCRIPTION OF THE DRAWINGS

In the drawings, wherein like reference numerals denote corresponding parts throughout the several views:

FIG. 1 is an oblique view, as seen from above, of a device embodying the invention shown in the assembled condition of use;

FIG. 2 is an "exploded" view of the device illustrated in FIG. 1, showing how the support frame is removably fitted into the fold at the upper end of the bag.

FIG. 3 is a side elevational view of a disposable bag embodying the invention, illustrating its method of construction;

FIG. 4 is a side elevational view similar to that of FIG. 3, but showing the completed fabrication of the bag;

FIG. 5 is a vertical, cross-sectional view of FIG. 4, taken along the line 5—5 thereof in the direction of the arrow; and FIG. 6 is a transverse cross-sectional view taken along the plane indicated at 6—6 of FIG. 1, in the direction of the arrows.

Referring now in detail to the drawings reference numeral 10 designates, generally, a preferred form of the invention, the same comprising a disposable bag 11 and a reusable bag support frame 12. As is hereinbelow more particularly described, the bag 11 is provided with a cuff-like fold 13 at its upper or open end, into which the two legs 14, 15 of the wishbone-like frame 12 can be removably inserted for its hanging support.

As illustrated in 3, 4 and 5, the bag 11 is of generally rectangular shape, and is fabricated of a thin, flexible, waterproof material. Preferably, the bag 11 will be made of a thin synthetic plastic sheet material having thermo-setting qualities enabling sealing into bag shape along the vertical edges 16, 17 and along the top fold 18, as is hereinafter more particularly described.

As illustrated in FIG. 3 in fabricating the bag 11, a short diagonal cut or slit 19 is made therein, extending inwardly of an upper corner thereof, whereafter, as illustrated in FIG. 4, the major separated upper end portion 20 (see FIG. 3) will be folded inside-out and down along the broken line 21. After this has been accomplished, the outer horizontally-extending edge portion of the fold 13 will be secured in place against the outsides of the bag, such as by heat sealing along seam 18 as described above. With such construction, it will be understood that, as illustrated in FIGS. 4 and 5, one end of the bag will be formed with an upwardly-extending, triangular finger grip portion 22 directly under which are a pair of opposed end openings 23, 24 extending interiorly of the fold 20 on each side of the bag.

FIGS. 1 and 2 illustrate how the legs 14, 15 of the wishbone-like frame 12 can be removably inserted within the fold openings 23, 24 of a disposable bag for hangingly supporting it for use. In this connection it is to be noted that the support frame 12 will preferably be integrally formed of a tough synthetic plastic material having a flat finger-grip handle portion 25, from which the legs 14, 15 extend symmetrically with such curvature as to define therebetween an elongate elipsoidal opening 26. The outer ends of the support frame legs 14, 15 are rounded, as indicated at 26, 27, respectively, and somewhat spaced from one another to afford easy access into the end openings 23, 24 of the bag for hangingly supporting the same. When fully inserted, as illustrated in FIG. 1, the bag is of such size in relation to that of the support frame 12, that the upper open end of the bag will assume substantially the same elipsoidal shape as that defined by the frame legs, with the triangular finger-grip portion 22 of the bag extending upwardly of the frame at the bight thereof.

In use, the supported bag will be held by the finger-grip portion 25 and placed at the crotch for receiving the flow of urine. The bag is large enough to hold at least 12 ounces of fluid. After urination is completed, the bag can conveniently be removed from the support frame 12 simply by gripping the triangular finger-grip portion 22 with the other hand and sliding it off, after which it can be disposed of such as by flushing down a toilet. It will be understood that the bag support frame 12 is reusable and of such compact size as to be storable in a woman's purse or the like, and that the disposable bags, being thin, highly flexible and inexpensive to manufacture, can be supplied in compact packets for storage with the support frame for ready use whenever required.

While I have illustrated and described herein only one form in which my invention can conveniently be embodied in practice, it is to be understood that this embodiment is presented by way of example only and not in a limiting sense.

What I claim and desire to secure by Letters Patent is:

1. A bag and hanger device comprising, in combination, a flexible, waterproof bag, open at one end, a substantially rigid frame member integrally formed with a finger-grip handle portion at one end extending into a pair of opposed, arcuate leg portions defining therebetween an elongate, elipsoidal opening, the ends of said legs being rounded and laterally spaced from one another, said bag, at its open end, having laterally extending openings in opposed marginal side portions thereof for the reception therein of one each of said leg portions of said frame member, whereby said bag will be hangingly supported by said frame member when inserted therein, said bag being fabricated of a rectangular sheet of flexible, waterproof material, folded double and sealed along opposed, vertical side edges so as to be open at its upper end, thereby providing for flat storage of the bag before use with the sides thereof in substantially face-to-face, abutting relation, a diagonal through cut in a marginal upper end portion of said bag extending inwardly of one corner thereof when in its flat position, said cut defining an upwardly-extending finger-grip portion at one side, at a remaining upper end marginal portion of said bag, said upper end marginal portion of said bag being folded down against opposed outer sidewall portions of said bag and attached along its outer edge against adjacent sidewall portions of said bag, thereby defining said laterally-extending openings.

2. A bag and hanger device as defined in claim 1 wherein said frame member is of wishbone shape and symmetrical with respect to its longitudinal axis.

3. A bag and hanger device as defined in claim 1 wherein the lateral length of said bag from end to end is only slightly greater than the length of the legs of said frame member, whereby, upon the insertion of said frame member legs in the laterally-extending openings of said bag, said finger-grip portion thereof will extend upwardly of the bight of said frame member and said flexible bag will be constrained to assume, at its upper end, an opening of elongate, elipsoidal shape as defined by said frame member legs.

* * * * *